United States Patent [19]

Chae et al.

[11] 4,182,899
[45] Jan. 8, 1980

[54] OPTICAL RESOLUTION OF AMINO ACIDS INTO OPTICAL ANTIPODES

[75] Inventors: Yung B. Chae; Dae W. Kim, both of Seoul, Rep. of Korea

[73] Assignee: Hoechst Aktiengesellschaft, Frankfurt am Main, Fed. Rep. of Germany

[21] Appl. No.: 931,529

[22] Filed: Aug. 7, 1978

[30] Foreign Application Priority Data

Aug. 9, 1977 [DE] Fed. Rep. of Germany ....... 2735834

[51] Int. Cl.$^2$ .................... C07C 69/02; C07C 101/06
[52] U.S. Cl. .................... 560/142; 260/390; 260/448.2 R; 260/501.11; 560/20; 560/30; 560/32; 560/33; 562/430; 562/434; 562/444; 562/449; 562/450; 562/451
[58] Field of Search .................. 260/501.11; 560/142, 560/16, 30, 32

[56] References Cited

U.S. PATENT DOCUMENTS

| | | | |
|---|---|---|---|
| 3,132,176 | 5/1964 | Bollinger et al. | 560/142 |
| 3,796,748 | 3/1974 | Holdrege | 260/501.11 |
| 3,869,505 | 3/1975 | Palmer | 260/501.11 |
| 3,904,681 | 9/1975 | Eichenberger et al. | 260/501.11 |
| 4,002,666 | 1/1977 | Shirai et al. | 260/501.11 |

FOREIGN PATENT DOCUMENTS

| | | | |
|---|---|---|---|
| 50-116434 | 11/1975 | Japan | 260/501.11 |
| 51-52154 | 8/1976 | Japan | 260/501.11 |

OTHER PUBLICATIONS

Greenstein & Winitz, Chem. of the Amino Acids, John Wiley & Sons, Inc., N.Y., vol. 1, pp. 715–728 (1961).
Radke et al., Chem. Absts., 49, 10186(d) (1955).
Mutak et al., Chem. Absts., 86, 190466(c) (1977).

*Primary Examiner*—James O. Thomas, Jr.
*Assistant Examiner*—G. T. Breitenstein
*Attorney, Agent, or Firm*—Curtis, Morris & Safford

[57] ABSTRACT

The present application relates to the optical resolution into optical antipodes of compounds of the formula

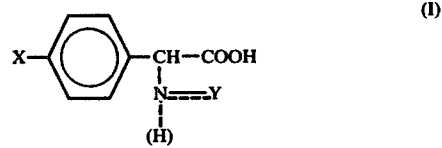

as well as to salts consisting of an optical isomer of a compound of the above formula and an optical isomer of 2-aminobutanol. The optically active compounds of the above formula are employed as starting materials for the production of semisynthetic antibiotics of the cephalosporin or penicillin type.

3 Claims, No Drawings

OPTICAL RESOLUTION OF AMINO ACIDS INTO OPTICAL ANTIPODES

This invention relates to the optical resolution into optical antipodes of compounds of the formula I

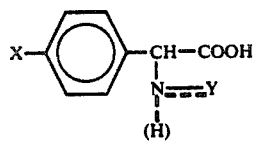

in which X is H; OH, $C_1$–$C_4$ alkoxy; aryloxy; $C_1$–$C_4$ acyloxy; aralkyloxy optionally substituted with a maximum of 3 halogen atoms or nitro groups and having a maximum of 4 carbon atoms in the alkyl moiety; tertiary-alkoxy with a tertiary carbon atom bound to the oxygen; or alkoxycarbonyloxy or picolyloxy-carbonyloxy and Y is aliphatic acyl optionally substituted by up to 3 halogen atoms or containing further carbonyl groups; acoyl optionally substituted by halogen; alkyl; alkoxy; nitro; phthalyl; trityl; benzylidene, optionally substituted by alkyl, alkoxy or halogen; acetylisopropylidene; benzoylisopropylidene; 5,5-dimethyl-3-oxo-cyclohexen-1-yl; trichlorethyloxycarbonyl; benzyloxycarbonyl optionally substituted by alkyl, alkoxy, halogen, nitro or -B(OH)$_2$; tertiary alkoxy with a tertiary carbon atom bound to the oxygen; adamantyloxy carbonyl; diphenylisopropyloxy carbonyl; fluorenyl-9-methyloxy carbonyl; methylsulfonylethyloxy carbonyl; 3,5-dimethoxyphenylisopropyloxy carbonyl; isobornyloxy carbonyl; nitrophenylsulfenyl; tosyl; dibenzylphosphoryl; diphenylphosphin or trimethylsilyl.

The optically active compounds of the above formula are employed as a starting material for the production of semisynthetic antibiotics of the cephalosporin or penicillin type, for example, Ampicillin or Amoxycillin. This invention provides a new process for obtaining the optically active compounds of the above formula by the use of optically active 2-aminobutanol.

According to one known process for the resolution of compounds into optical isomers of the above formula, optically active natural amines such as cinchonidine or dehydroabietyl amine have been used. However, these natural amines are very expensive, and the resolution yields when these amines are used are still poor. In addition to these disadvantages, recycling of these natural amines for reuse is limited because considerable amounts of these amines are destroyed during the resolution which is carried out at high temperatures.

According to the present invention, the amino group of the amino acid or one of its derivatives is substituted to increase the acidity of the amino acid. The amino acid derivatives thus obtained form the salts more easily with 2-aminobutanol than the amino acids themselves. Salt formation is usually carried out in water or a lower alkanol, preferably methanol, ethanol or isopropanol, to precipitate one of the two salts which can be formed from a racemic compound of the formula I and optically active 2-aminobutanol.

This invention is superior to known processes in that the optical purity is more than 99% and higher yields are obtained.

Optionally the amino acid derivatives are converted to the amino acid or to an amino acid substituted at either the amino group or the phenyl ring.

This invention is further illustrated by the following examples:

EXAMPLE 1

Salt of l-N,O-diacetyl-4-hydroxy-phenylglycine with l-2-aminobutanol.

l-2-Aminobutanol (18 g) is added to a suspension of dl-diacetyl-4-hydroxy-phenylglycine (47.5 g) in 400 cc of ethanol with stirring. The reaction mixture is slowly heated to give a solution. The resulting solution is cooled to room temperature, and allowed to stand for 2 hours to complete precipitation of the salt. The salt is collected by filtration and 30 g of a crude product is obtained. By recrystallization from 80 cc of ethanol, the pure salt of l-N,O-diacetyl-4-hydroxyphenylglycine with l-2-aminobutanol is obtained, m.p. 168°–170° C. and $(\alpha)_D^{25} = -126°$ (C=2, H$_2$O).

l-4-hydroxyphenylglycine

The salt obtained in the above procedure is treated by a known method to give l-4-hydroxyphenylglycine having an optical purity ($[\alpha]_D^{25} = -159°$ (C=2, N-HCl) of more than 99%.

EXAMPLE 2

Salt of l-N-acetyl-4-methoxy-phenylglycine with l-2-aminobutanol.

l-2-Aminobutanol (1.8 g) is added to a suspension of dl-diacetyl-4-methoxy-phenylglycine (4.46 g) in 15 cc of absolute methanol. The process is carried out according to Example 1 to obtain the crude salt (3.1 g) of l-N-acetyl-4-methoxy-phenylglycine with l-2-aminobutanol. The pure salt is obtained by recrystallization from 5 cc of absolute methanol. 2.5 g (80%): $[\alpha]_D^{25} = -107°$ (C=2, H$_2$O).

What is claimed is:

1. A salt formed between an optical isomer of 2-aminobutanol and an optical isomer of a compound of the formula

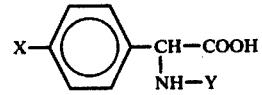

where X is $C_1$–$C_4$ alkoxy or $C_1$–$C_4$ aliphatic acyloxy and Y is aliphatic acyl.

2. A salt as in claim 1 wherein said compound is N,O-diacetyl-4-hydroxy-phenylglycine.

3. A salt as in claim 1 wherein said compound is N-acetyl-4-methoxy-phenylglycine.